United States Patent [19]

Fields

[11] Patent Number: 5,017,193

[45] Date of Patent: May 21, 1991

[54] INFANT FEEDING DEVICE

[75] Inventor: Charlie B. Fields, Ypsilanti, Mich.

[73] Assignee: Tri-State Hospital Supply Corp., Howell, Mich.

[21] Appl. No.: 478,289

[22] Filed: Feb. 9, 1990

Related U.S. Application Data

[63] Continuation-in-part of Ser. No. 249,430, Sep. 26, 1988, abandoned.

[51] Int. Cl.[5] .......... A61M 31/00

[52] U.S. Cl. .......... 604/270; 604/280

[58] Field of Search .......... 604/54, 257, 264, 270, 604/280; 128/658; 606/191-194

[56] References Cited

U.S. PATENT DOCUMENTS

| | | | |
|---|---|---|---|
| 4,692,152 | 9/1987 | Emde | 604/270 |
| 4,698,059 | 10/1987 | Johnson | 604/270 |
| 4,704,111 | 11/1987 | Moss | 604/270 |
| 4,778,455 | 10/1988 | Kousai et al. | 604/270 |

FOREIGN PATENT DOCUMENTS

| | | |
|---|---|---|
| 2810326 | 6/1979 | Fed. Rep. of Germany . |
| 3105883 | 2/1981 | Fed. Rep. of Germany . |
| 1477803 | 6/1979 | United Kingdom . |

*Primary Examiner*—C. Fred Rosenbaum
*Assistant Examiner*—William Lewis
*Attorney, Agent, or Firm*—Brooks & Kushman

[57] ABSTRACT

An infant feeding device (10) disclosed includes a flexible elongated tube (12) including a longitudinal bore (14) therethrough for delivering liquid into the stomach of an infant. The tube (12) has an inlet (16) which is connected to a reservoir of the liquid, an intermediate portion (18), and an outlet (20) which includes a plurality of the laterally extending ports (22) so that the liquid may be delivered outwardly therethrough into the infant's stomach. A pliable plastic tip (24) including a cavity (30) having a fluid therein is affixed to the outlet (20) and protects delicate membranes and tissues of the infant as the feeding device is inserted into the nasogastric passages.

7 Claims, 1 Drawing Sheet

INFANT FEEDING DEVICE

CROSS-REFERENCE TO RELATED APPLICATION

This application.,is a continuation-in-part of application Ser. No. 249,430, filed Sept. 26, 1988, now abandoned.

TECHNICAL FIELD

This invention relates generally to feeding devices and more particularly to feeding devices which are used for delivering food through the nasogastric passages of an infant.

BACKGROUND ART

Until recently, most patients requiring tube feedings were fed by plastic or rubber, large-bore nasogastric tubes. Unfortunately, when used for a prolonged period, these tubes irritate the nasopharynx, esophagus, and stomach. During the 1970's, soft, small-bore feeding tubes were made of polyurethane or silicone because they could be placed through the nares into the stomach or upper small intestine with minimal discomfort to the patient. Although the incidence of mechanical irritation to nares, stomach, and duodenum has been greatly reduced by the newer tubes, there still remain problems associated with their use. Such problems include the ease of dislocating the feeding tube, particularly during coughing or vomiting. Additionally, accidental upward displacement of the tip of the tube from its original intended position (either in the stomach or the intestine) can place the patient at risk.

Conventional feeding tubes have been made of very hard plastic or hard rubber hoses so that they can be inserted into the stomach to support nutrition. Stiff needle-like objects, called stylettes were often used to lend rigidity to the tube to facilitate its placement. After insertion of the feeding tube, the stylette would then be removed. However, the stylette would sometimes come out of the tube, puncture, and injure the patient.

Other approaches involve the use of a weighted tube which has a bolus of mercury or tungsten attached at the distal tip. This approach, however, brings with it the risk of causing trauma to the infant because the tip must pass between very delicate tissues in the nasal cavity and in the esophagus. As a result, internal bleeding may follow which may lead to enterocolitis, which is infection and inflammation of the feeding tract. Even tubes with heavy mercury weights can be relocated during bouts of severe abdominal coughing.

U.S. Pat. No. 4,778,455 discloses combining a metal material within synthetic resin tip material to provide a weighted tip without the risk of trauma associated with a bolus of metal. However, the composite resulting from this combination is less elastic than the initial synthetic resin and less acceptable.

Pliable small-bore tubes may be inserted under fluoroscopy by a radiologist, or may be inserted by nurses or physicians. However, the need arises to ensure proper positioning of such tubes before feedings are initiated. At present, no consistently reliable method other than radiography can confirm the placement of these tubes. Accordingly, there has arisen a need for position-indicating indicia to enable the determination and monitoring of tube placement.

Against this background, the need has arisen to manufacture and distribute an infant feeding tube, the position of which can easily be determined, which is stiff enough to insert, but without having a stylette inside. Ideally, the stiffer the better, for ease of insertion. Additionally, with the high costs of medical care, there has arisen a need for an infant feeding tube which is inexpensive, can be used once, and then thrown away.

DISCLOSURE OF INVENTION

An object of the present invention is to provide an infant feeding device has particular utility in connection with feeding infants.

Another object of the invention is to provide an infant feeding device that includes a tip which reduces complications associated with insertion and removal of the tube.

In carrying out the above object, the infant feeding device of the present invention comprises a flexible, elongated tube including a longitudinal bore therethrough for delivering liquid foodstuff into the stomach of the infant. The elongated tube has an inlet which communicates the tube to a reservoir of the liquid. Connected to the inlet is an intermediate portion for delivering liquid through the bore. An outlet, including a terminal end, is connected to the intermediate portion, the outlet includes a plurality of laterally extending ports connected to the bore. The ports deliver the liquid outwardly into the stomach of the infant after insertion of the feeding device. A pliable plastic tip is affixed to the outlet, the pliable tip protects delicate membranes and tissues of the infant as the feeding device is inserted into and removed from the nasogastric passages.

To provide softness to the plastic tip and protection to the delicate membranes and tissues of the infant upon insertion of the feeding device, the tip includes a sleeve portion for mounting it on the tube outlet and a probe portion connected to the sleeve portion. An annular rib between the sleeve and probe portions provides a seat for abutting engagement between the terminal end and annular rib. The probe portion defines a hollow cavity therewithin of sufficient volume and having a fluid therein to impart sufficient pliability to the plastic. The probe portion also defines a throat portion connected to the hollow cavity.

In a first embodiment of the invention the hollow cavity is in fluid communication with the tube whereby liquid in the tube defines the fluid in the cavity. In a second embodiment of the invention the device also includes a plug member sealingly mounted in the tube outlet to seal off the hollow cavity. The hollow cavity is charged with a gaseous fluid to thereby form a cushioned tip.

In both embodiments of the infant feeding device, the plurality of laterally extending ports comprises a pair of ports connected to the bore proximate the tip, the ports being disposed on opposing sides of the tube. As a result, the liquid may be delivered and distributed outwardly through the ports from opposing sides of the feeding device.

Also in the preferred embodiment, the feeding device includes positioning indicia so that the position of the feeding device in the nasogastric passages can be determined and monitored during feeding.

The objects, features, and advantages of the present invention are readily apparent from the following detailed description of the best mode for carrying out the invention when taken in connection with the accompanying drawings.

BEST MODE FOR CARRYING OUT THE INVENTION

Figure 1:
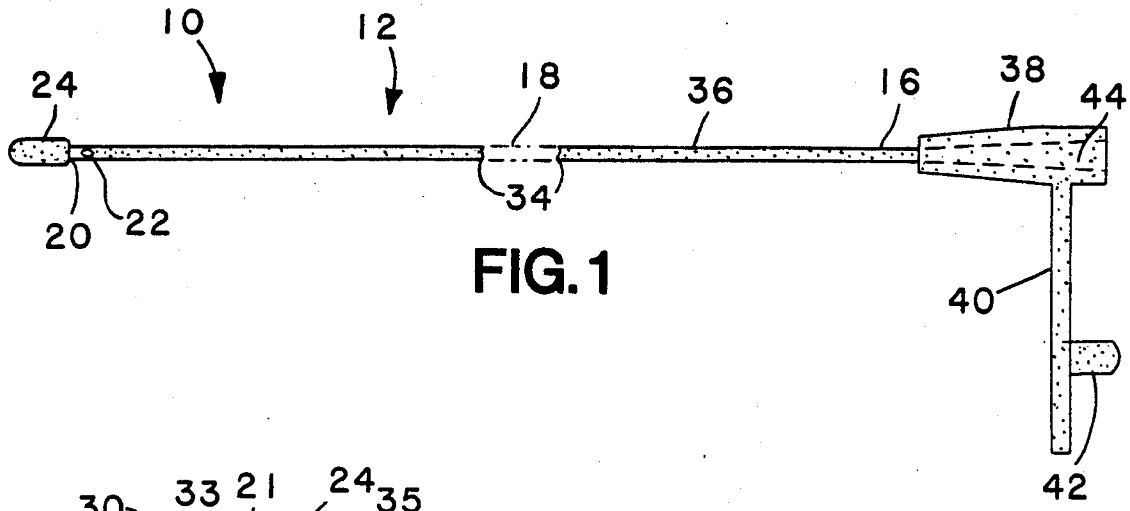
FIG. 1 is a plan view of a feeding device constructed in accordance with the present invention.

Referring to FIG. 1 of the drawings, there is shown an infant feeding device 10 for nasogastric feeding. The infant feeding device 10 comprises a flexible elongated plastic tube 12 including a longitudinal bore 14 therethrough for delivering such liquid foodstuff as formula or breast milk into the stomach of the infant. The elongate tube 12 has an inlet 16 for linking the tube 12 to a reservoir of the liquid (not shown). Connected to the inlet 16 is an intermediate portion 18 for delivering liquid through the bore 14. Downstream, an outlet 20 is connected to the intermediate portion 18. The outlet 20 includes a terminal end 21. So that the liquid may be delivered outwardly into the stomach of the infant, the outlet 20 includes a plurality of laterally extending ports 22. The ports 22 are smooth, and free of burrs and sharp edges. Superior results have been obtained where the ports 22 are located about 0.250 inches from each other, with the port 22 closest to the outlet 20 being about 0.350 inches therefrom.

Figure 3:
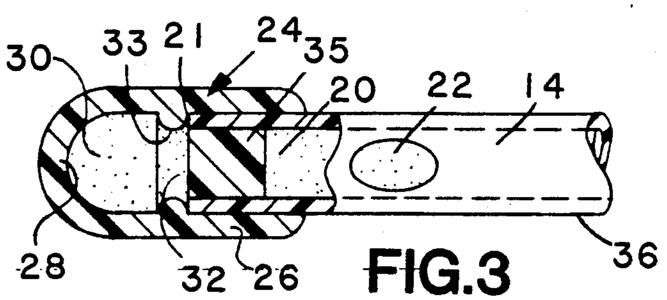
FIG. 3 is a sectional view of the tip of the infant feeding device constructed in accordance with a second embodiment of the invention.
Figure 2:
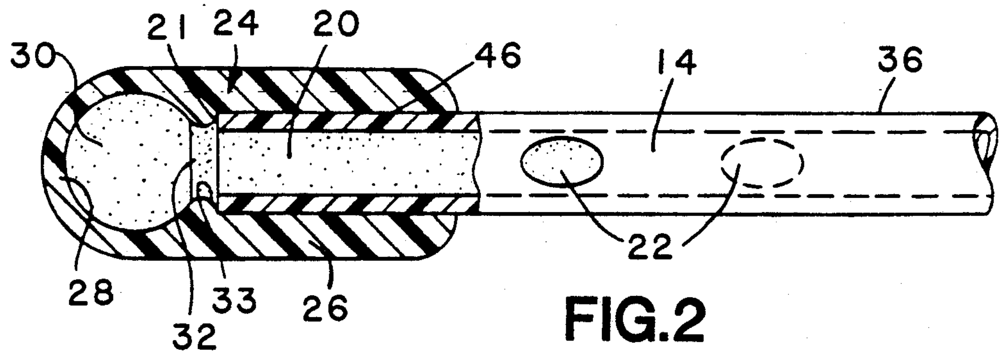
FIG. 2 is a sectional view of a tip of the feeding device constructed in accordance with a first embodiment of the present invention.

With reference to FIGS. 2 and 3 of the drawings, a pliable plastic tip 24 is affixed to the outlet 20 of the tube 12, the pliable tip 24 protects delicate membranes and tissues of the infant as the feeding device 10 is inserted into and removed from the nasogastric passages. The pliable tip 24 further comprises a sleeve portion 26 for receiving the outlet 20 of the tube 12. Connected to the sleeve portion 26 is a probe portion 28 which defines a hollow cavity 30 therewithin. Hollow cavity 30 is of sufficient volume and has a fluid therein to impart sufficient pliability to the plastic. Probe portion 28 also defines a throat portion 32.

FIG. 2 illustrates a first embodiment of the invention wherein the hollow cavity 30 is in fluid communication with the elongated tube 12. An annular rib 33, therebetween the sleeve portion 26 and the probe portion 28, provides a seat for abutting engagement with the terminal end 21 of the tube 12. This construction prevents the tube 12 from being pushed up into the hollow cavity 30 of the probe portion 28 which would defeat the function of the pliable tip 24. Therein the first embodiment, the liquid in tube 12 defines the fluid in hollow cavity 30.

FIG. 3 illustrates a second embodiment of the invention wherein a plug member 35 is sealingly mounted in outlet 20. Plug member 35 seals the hollow cavity 30 from outside fluid communication. In this second embodiment, hollow cavity 30 is charged with a gaseous fluid to thereby form a cushioned tip 24.

In operation, the hollow cavity 30 and the throat portion 32 cushion the pliable tip 24 of the feeding device 10 as the feeding device 10 is inserted into and removed from the nasogastric passages. This cushioning reduces complications associated with feeding tube use.

It has been found that the cavity 30 has an internal radius of about 0.044 inches, with about 0.014 inches of material defining the hollow cavity proximate the probe portion 28. In operation, the hollow cavity 30 and the throat portion 32 pillow the pliable tip 24 of the feeding device 10 during insertion and removal. Average dimensions for the tip 24 disclosed include an outside sleeve diameter of about 0.115 inches, and a length of the sleeve portion 26 of about 0.145 inches.

In the particular device illustrated, the plurality of laterally extending ports 22 are connected to the bore 14 proximate the tip 24. In this embodiment, the ports 22 are disposed on opposing sides of the tube 12 so that the liquid may be delivered and distributed outwardly through the ports 22 from opposing sides of the feeding device 10 after its insertion into the nasogastric passages.

The infant feeding device 10 of the present invention includes positioning indicia 34 so that position of the feeding device 10 in the nasogastric passages can be determined and monitored during insertion, feeding, and removal. As also illustrated in FIG. 1, the feeding device 10 also includes a radio-opaque stripe 36 located generally parallel to the bore 14 so that the feeding device 10 is visible through fluoroscopy equipment.

It has been found convenient to include positioning indicia 34 beginning at about 7.9 inches from the outlet 20 of the tube 12. In practice, the radio-opaque stripe 36 comprises about 20 percent barium sulphate or bismuth trioxide.

In the embodiment illustrated in FIG. 1, the feeding device 10 also includes a luer slip adaptor 38 connected to the inlet 16 of the tube 12 for delivering the liquid from the reservoir (not shown) into the bore 14 of the tube 12 proximate the inlet 16. The luer slip adaptor 38 includes a flexible arm 40 and a pin 42 connected to the arm 40. Defined within the luer slip adaptor 38 is an orifice 44 which receives the pin 42 so that the adaptor 38 is reclosable after feeding. It has been found that a useful length from the luer slip adaptor 38 to the outlet 20 is about 15 inches.

Turning now to FIGS. 2 and 3, the pliable tip 24 is premanufactured prior to connection to the tube 12. Good results have been achieved where the length of the tip 24 is about 0.250 inches.

In the embodiments illustrated in FIGS. 2 and 3, the pliable tip 24 is formed by immersing the outlet 20 in a bath of fluid, curable plastic. While the rest of the tube 12 is produced from a relatively stiff material, the pliable tip 24 is made from a PVC compound called "plastisol." "Plastisol" is a solution grade of PVC, and may be in solution with such other solvents as toluene and cyclohexanone which will dissolve the PVC. As a substitute for PVC, polyurethane or polyethylene compounds may be used. As shown in FIGS. 2–3, the infant feeding device 10 includes an in-situ molded solvent bond 46 for affixing the tip 24 to the outlet 20 of the tube 12.

In practice, the plastisol material used for dipping must be of medical grade, biocompatible, and be soft (20–30 durometer, shore A scale). In contrast, the material from which the tube 12 is fabricated has a durometer of approximately 80 shore A.

While there are many types of plastisols, the preferred compound is one that cures at lower temperatures. Under this approach, the tip is dipped into the plastisol material, and then cured at a temperature, such as room temperature, that does not damage the tubing or cause it to coil. Coiling is very undesirable, as the "coil memory" would make a feeding tube difficult to insert. By curing in this fashion, the device 10 avoids the tendency of conventional feeding devices to coil in the back of the throat and enter the trachea.

Alternatively the pliable tip 24 is premanufactured from medical grade, biocompatible materials of a low durometer. Such materials may be plastisol, but higher temperatures (approximately 400° F.) may be used. It has been found that the higher temperature speeds production of the parts, thereby lowering their cost of production. Operating experience has shown that any medical grade, biocompatible PVC resin can be used, providing it meets the softness requirements. Such premanufactured tips may then be solvent-bonded or welded to the outlet 20 of the tube 12. Solvents found acceptable for use include cyclohexanone and tetrahydrofuran.

In practice, where the tip is pre-molded, the tip 24 is melted onto the tube 12 so that the tip 24 and the tube 12 are fused together. In this way, there is little risk of the tip 24 coming apart from the tube 12. Superior results have been obtained by first moistening the tube 12 with the solvent, and then wiping off the excess solvent so that the outlet 20 of the tube 12 is coated with a film of the solvent. Within about five seconds, the outlet 20 softens and becomes melted. Then, the tip 24 and the outlet 20 are joined. The two become affixed to each other in only a couple of seconds, after which they become fused. It has been found that the longer the tip 24 and the outlet 20 are fused, the stronger the bond becomes, with the maximum retention being realized after about four days.

After insertion of the outlet 20 of the tube 12 into the tip 24, a small cushion of air becomes trapped inside the tip 24, which results in the formation of the cavity 30 and throat portion 32. Together, the cavity 30 and throat portion 32 cooperate to provide a pillow or cushion effect as the infant feeding device 10 is deployed.

In practice, it has been found that the difference between the outside diameter of the tube 12 and the inside diameter of the tip 24 is about 0.002 inches. In one embodiment, good results have been achieved where the outside diameter of the tube 12 is of the order of 0.065 inches and the inside diameter of the tip 24 is about 0.063 inches.

The infant feeding device 10 can be made by a method which includes the steps of cutting the tube 12 to a desired length, and then marking the intermediate portion 18 of the tube 12 with the positioning indicia 34. The luer slip adaptor 38 is then attached to the inlet 16 of the tube 12. At the outlet 20 of the tube 12, the pliable tip 24 is attached so that the pliable tip 24 protects the membranes and tissues of the nasogastric passages as the feeding device is inserted into and removed from the infant. Finally, laterally extending ports 22 are cut into the tube 12 proximate the outlet 20 for delivering liquid.

Using the device disclosed and claimed herein, the device 10 is suitable for short term, i.e. less than forty-eight (48) hours intubation.

The infant feeding device 10 disclosed is relatively inexpensive to produce, costing less than $1.00 per unit. Additionally, the feeding device 10 satisfies the reed to monitor accurately position and placement by including positioning indicia 34 which ensure proper tip placement. Ports 22 near the tip 24 on opposing sides of the tube 12 allow the liquid to be distributed relatively evenly on opposing sides of the tube 12.

While the best mode for carrying out the invention has been described in detail, those familiar with the art to which this invention relates will recognize alternative ways of practicing the invention as defined by the following claims.

What is claimed is:

1. An infant feeding device for nasogastric feeding, the feeding device comprising:

a flexible, elongated tube including a longitudinal bore therethrough for delivering liquid into the stomach of the infant, the elongated tube having an inlet for communicating the tube to a reservoir of the liquid, an intermediate portion connected to the inlet for delivering liquid through the bore, and also having an outlet including a terminal end connected to the intermediate portion, the outlet including a plurality of laterally extending ports communicated to the bore so that the liquid may be delivered outwardly through the ports into the stomach of the infant after insertion of the feeding device into the nasogastric passages of the infant;

a plug member sealingly mounted in said terminal end of the outlet;

a pliable plastic tip affixed to the terminal end of the tube; the tip including a sleeve portion mounting the tip on the terminal end of the tube, an annular rib adjacent the sleeve portion providing a seat for abutting engagement with the terminal end, a probe portion connected to the sleeve portion with the annular rib therebetween, the probe portion defined by a cavity therewithin of sufficient volume and being charged with gaseous fluid therein to impart sufficient pliability to said plastic, the cavity providing cushioning for the pliable tip thereby protecting delicate membranes and tissues of the infant as the feeding device is inserted into and removed from the nasogastric passages.

2. The infant feeding device of claim 1 wherein the plurality of laterally extending ports comprises a pair of laterally extending ports connected to the bore proximate the tip, the ports being disposed on opposing sides of the tube so that the liquid may be delivered and distributed outwardly through the ports from opposing sides of the feeding device after insertion of the feeding device into the nasogastric passages of the infant.

3. The infant feeding device of claim 1 wherein the intermediate portion of the feeding device includes positioning indicia so that the position of the feeding device in the nasogastric passages can be determined and monitored during insertion, feeding and removal of the feeding device.

4. The infant feeding device of claim 1 wherein the feeding device also includes a radio-opaque stripe located generally parallel to the bore so that the feeding device is visible through fluoroscopy equipment.

5. The infant feeding device of claim 1 wherein the feeding device also includes a luer slip adaptor connected to the inlet of the tube for delivering the liquid from the reservoir into the bore of the tube, the luer slip adaptor being reclosable after feeding.

6. The infant feeding device of claim 1 wherein the pliable tip is premanufactured prior to connection to the tube.

7. The infant feeding tube of claim 6, wherein the infant feeding device also includes an in situ molded solvent bond for affixing the tip to the outlet of the tube.

* * * * *